US006884602B2

(12) United States Patent
Mueller et al.

(10) Patent No.: US 6,884,602 B2
(45) Date of Patent: Apr. 26, 2005

(54) EXPRESSION OF ALKALINE PHOSPHATASE IN YEAST

(75) Inventors: Rainer Mueller, Penzberg (DE); Johann-Peter Thalhofer, Weilheim (DE); Frank Geipel, Penzberg (DE); Werner Hoelke, Penzberg (DE); Stephan Glaser, Seeshaupt (DE); Hellmut Eckstein, Weilheim (DE); Thomas Kirschbaum, Munich (DE); Bettina Bommarius, Atlanta, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 09/911,132

(22) Filed: Jul. 23, 2001

(65) Prior Publication Data

US 2003/0096341 A1 May 22, 2003

(30) Foreign Application Priority Data

Jul. 25, 2000 (DE) .......................... 100 36 491

(51) Int. Cl.$^7$ .................... C12P 21/06; C12N 15/74; C12N 1/14; C12N 1/16; C07K 1/00
(52) U.S. Cl. .................. 435/69.1; 435/69.2; 435/320.1; 435/483; 435/255.1; 435/255.5; 435/255.6; 435/254.2; 530/355
(58) Field of Search .......................... 435/255.1, 255.5, 435/255.6, 69.1, 320.1, 254.2, 69.2, 252.3, 252.33, 172.3; 530/350, 403

(56) References Cited

FOREIGN PATENT DOCUMENTS

| EP | 0399455 | 11/1990 | ........... C12N/15/14 |
|----|---------|---------|---------------------|
| EP | 0700997 A1 | 3/1996 | ........... C12N/15/12 |
| EP | 0955369 A2 | 11/1999 | ........... C12N/15/55 |
| GB | 2200118 A | 7/1988 | ........... C12N/15/00 |
| WO | WO 99/04014 | 1/1999 | ........... C12N/15/53 |
| WO | WO 00/56900 | 9/2000 | ........... C12N/15/63 |
| WO | WO 01/66693 A1 | 9/2001 | ........... C12N/1/19 |

OTHER PUBLICATIONS

Reinhard, Beck et al, " Expression of Human Placental Alkaline Phosphatase in *Escherichia coli*", Protein Expression And Purification 5, 192–197 (1994).
Batard, Yannick et al., "Increasing Expression of P450 and P450–Reductase Proteins from Monocots in Heterologous Systems," Archives of Biochemistry and Biophysics, vol. 379, No. 1, Jul. 1, pp. 161–169, 2000.
Clare, Jeffrey J. et al., "Production of mouse epidermal growth factor in yeast: high–level secretion using *Pichia pastoris* strains containing multiple gene copies," Gene, 105 (1991) 205–212.

Li, Hong et al., "The Relation between Codon Using, Base Correlation and Gene Expression Level in *Escherichia coli* and Yeast," J. Theor. Biol. (1996) 181, 111–124.
Linder, Stefan et al., "Expression of Reticulomyxa filosa tubulins in *Pichia pastoris*: regulation of tubulin pools," FEBS Letters 417 (1997) 33–37.
Sreekrishna, Koti et al., "Stategies for optimal synthesis and secretion of heterologous proteins in the methylotrophic yeast *Pichia pastoris*," Gene 190 (1997) 55–62.
Zhao, X et al., " Synonymous condon usage in *Pichia pastoris*," Database Public Medline 'Online! NCBI; PMID: 11059269, May 2000.
Joel Berger, et al., "Expression of Active, Membrane–Bound Human Placental Alkaline Phosphatase by Transfected Simian Cells", Proc. Natl. Acad. Sci., USA vol. 84, pp. 4885–4889, Jul. 1987, Biochemistry.
James M. Cregg, et al., "*Pichia Pastoris* as a Host System for Transformations" Molecular and Cellular Biology, Dec. 1985, p. 3376–3385, vol. 5, No. 12.
T.R. Davis, et al., "Baculovirus Expression of Alkaline Phosphatase as a Reporter Gene for Evaluation of Production, Gycosylation and Secretion"Biotechnology, vol. 10, Oct. 1992 (p. 1148–1150).
Harry Harris, " The Human Alkaline Phosphatases: Whate We Know and What We Don't Know" Clinica Chemica Acta, 186 (1989) 133–150.
Thomas Manes, et al. "Genetic Complexity, Structure, and Characterization of Highly Active Bovine Intestinal Alkaline Phosphatases", The Journal of Biological Chemistry, vol. 273, No. 36, Issue of Sep. 4, pp. 23353–23360, 1998.
Robert B. McComb, et al., (1979) in Alkaline Phosinhatases, Plenum Press, New York and London (158pgs).
Jose Luis Millan, "Oncodevelopmental Expression and Structure of Alkaline Phosphatase Genes" Anticancer Research 8: 995–1004 (1988).
Robert K. Scopes, "Protein Purification" PA0007/002/003, Springer–Verlag, New York, Heidelberg Berlin, London, Paris, Tokyo (9pgs).
Heige Weissig, et al. "Cloning and Expression of the Bovine Intestinal Alkaline Phosphatase Gene: Biochemical Characterization of the Recombinant Enzyme" Biochem J. (1993) 290, 503–508, Printed in Breat Britain.

*Primary Examiner*—Gerry Leffers
*Assistant Examiner*—Maria Marvich
(74) *Attorney, Agent, or Firm*—Marilyn Amick; Roche Diagnostics Operations, Inc.

(57) ABSTRACT

This invention involves a process for selecting and producing eukaryotic alkaline phosphatase in yeast. Yeast cells are subjected to multiple transformations using a vector comprising a first resistance marker gene and the alkaline phosphatase gene. Those strains that grow in media containing the first resistance marker are further transformed using a vector comprising a second selection marker gene and the alkaline phosphatase gene. Transformants that grow in media containing the second selection marker are selected for expressing the eukaryotic alkaline phosphatase.

7 Claims, 3 Drawing Sheets

EXPRESSION OF ALKALINE PHOSPHATASE IN YEAST

Figure 1:
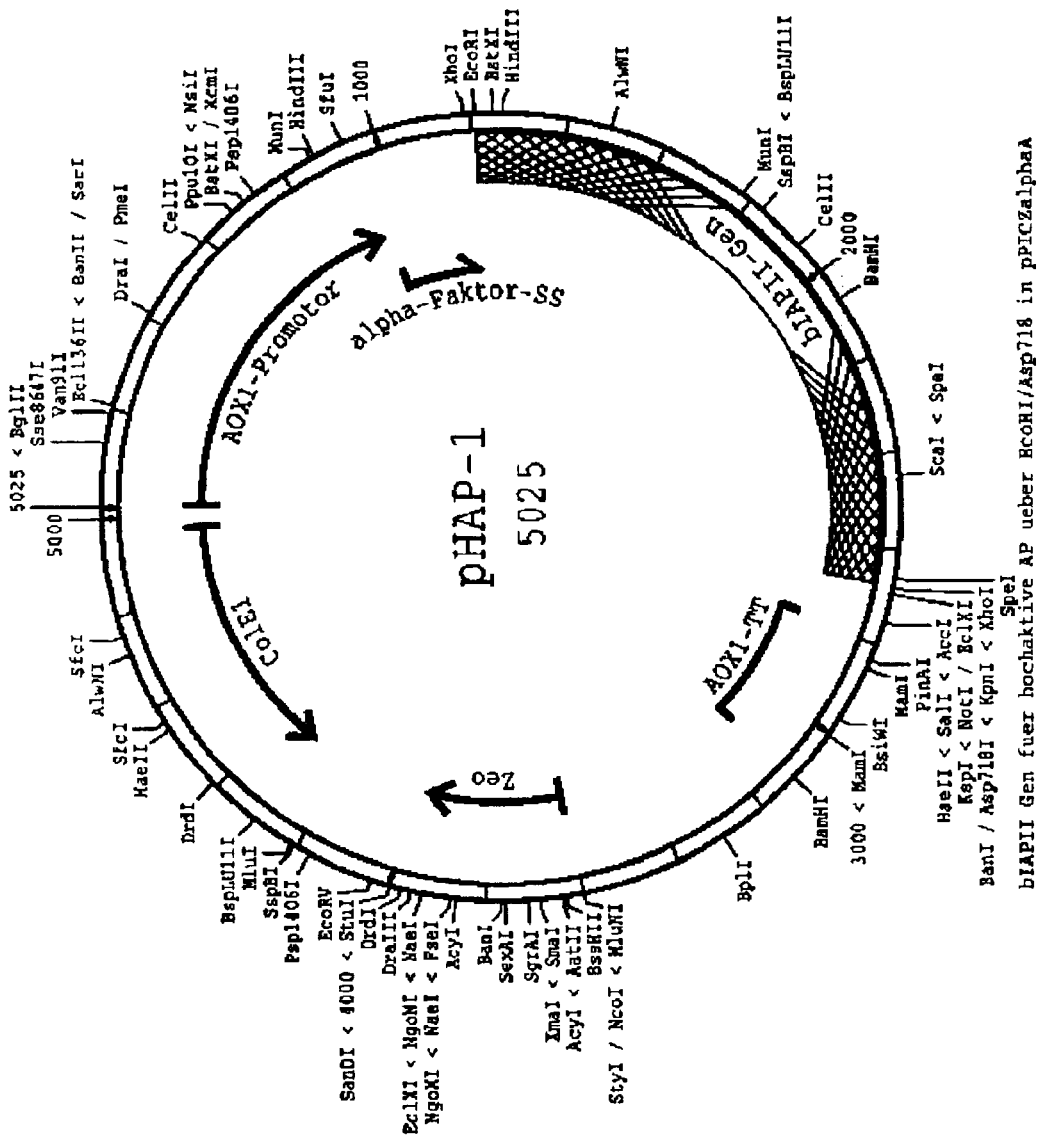

The invention concerns a process for the recombinant production and expression of eukaryotic alkaline phosphatase. The invention additionally concerns a codon-optimized DNA which codes for a eukaryotic highly active alkaline phosphatase having a specific activity of more than 3000 U/mg. Furthermore the invention concerns a process for inserting the DNA into a vector for expression in yeast cells.

Alkaline phosphatases (AP) are dimeric, zinc-containing, non-specific phosphomonoesterases which occur in prokaryotic as well as in eukaryotic organisms e.g. in *E. coli* and mammals (McComb et al., 1979 *Alkaline Phosphatases* Plenum Press, New York). Comparison of the primary structures of various alkaline phosphatases showed a high degree of homology (25–30% homology between *E. coli* and mammalian AP; Millan, 1988 *Anticancer Res.* 8, 995–1004; Harris, 1989 *Clin. Chim. Acta* 186, 133–150).

In humans and higher animals the AP family comprises four members that are located in different gene loci (Millan, 1988 *Anticancer Res.* 8, 995–1004; Harris 1989 *Clin. Chim. Acta* 186, 133–150). The alkaline phosphatase family includes the tissue-specific APs (placental AP (PLAP), germ cell AP (GCAP) and intestinal AP (IAP)) and the non-tissue specific APs (TnAP) which are primarily located in the liver, kidney and bones.

A decisive property of the previously known APs is the large variability of the catalytic activity of mammalian APs which have a 10-100-fold higher $k_{cat}$s value than *E. coli* AP. Among the mammalian APs, the APs from the bovine intestine (bIAP) exhibit the highest specific activities. This property makes the bIAPs attractive for biochemical applications such as the use of corresponding enzyme conjugates as a diagnostic reagent, or to dephosporylate DNA. The existence of various alkaline phosphatases from the bovine intestine having specific activities of varying magnitudes is described in EP 0 955 369 and Manes et al. (1998), *J.Biol.Chem.* 273 No. 36, 23353–23360. Up to now recombinant expression of eukaryotic alkaline phosphatases of low activity (up to 3000 U/mg) has been described in various eukaryotic cell lines such as CHO cells (bIAP I/WO 93/18139; Weissig et al. 1993, *Biochem. J.* 260, 503–508), COS cells (human placental AP/Berger et al., 1987, *Biochemistry* 84, 4885–4889) or baculovirus expression systems (human placental AP/Davis et al. 1992, *Biotechnology* 10, 1149–1150). The expression of more active APs (specific activity >3000 U/mg) from the bovine intestine in CHO cells has also been described (bIAP II, III and IV/Manes et al. 1998, *J. Biol. Chem.* 273 No. 36, 23353–23360). However, a disadvantage of expressing alkaline phosphatases in these expression systems is the low expression output which makes the recombinant production especially of a highly active AP uneconomic.

Although it is in principle possible to express eukaryotic alkaline phosphatases in prokaryotic expression hosts such as *E. coli* (human placental AP/Beck and Burtscher, 1994 *Protein Expression and Purification* 5, 192–197), the alkaline phosphatases expressed in prokaryotes are not glycosylated which is essential especially for preparing enzyme conjugates.

Consequently the object of the present invention is to develop a robust and stable expression process for the production of glycosylated eukaryotic alkaline phosphatase having a high specific activity, which, due to the high expression output, allows an economic production of such an alkaline phosphatase and, moreover, yields an enzyme whose properties are comparable to native alkaline phosphatase of high activity or low activity (commercially available for example from Roche Diagnostics GmbH, Biozyme, Oriental Yeast) with regard to for example specific activity and thermostability.

The object is achieved according to the invention by a process for the production of a eukaryotic alkaline phosphatase having a high specific activity in yeast and especially in a methylotrophic yeast comprising the steps:

a) cloning a gene sequence into different vectors
b) transformation of the yeast,
c) expression and
d) purification of the alkaline phosphatase, characterized in that
   (i) a first vector has a resistance gene for a first selection marker
   (ii) transformants which have integrated the resistance gene and the gene sequence into the genome are selected by growth on nutrient medium containing a low concentration of a first selection marker,
   (iii) gene copy number is increased by multiple transformation in which multiple transformants are selected by growth on a nutrient medium at an increased selection pressure,
   (iv) a second vector is added which has a resistance gene for a second selection marker in addition to the gene sequence,
   (v) the gene copy number is increased by multiple transformation with the second vector in which multiple transformants are selected by growth on nutrient medium at an increased selection pressure and
   (vi) the clones are selected which have integrated several copies of the gene sequence and the selection marker resistance genes into the genome in a stable manner.

A preferred gene sequence is a DNA sequence which codes for a eukaryotic alkaline phosphatase that has a specific activity of more than 3000 U/mg and in special cases of more than 7000 U/mg to about 10,000 U/mg. For example a DNA sequence according to SEQ ID NO: 1 has proven to be suitable according to the invention. A codon-optimized DNA sequence which corresponds to the gene sequence SEQ ID NO: 1 at the amino acid level is particularly preferred. Codon-optimization means that each codon for example of SEQ ID NO: 1 has been optimized by silent mutations i.e. changes at the DNA level which, however, have no effect at the amino acid level in order to increase the translation according to the requirements of the selected expression host which results for example in the gene sequence according to SEQ ID NO: 5. It is, however, also possible to incorporate other sequences than SEQ ID NO: 1 into the vector which code for alkaline phosphatases and are optionally codon-optimized such as bIAPI, III, IV (DE 198 19 962 and EP 0 955 369). It is particularly preferable for the process according to the invention to use a codon-optimized gene sequence according to SEQ ID NO: 5. The corresponding gene sequence is then cloned into one or several vector (s) which is or are selected depending on the host to be transformed.

Methylotrophic yeasts e.g. *Pichia pastoris* yeast, *Hansenula polymorpha* and also other yeasts such as *Saccharomyces cerevisiae*, *Yarrowia lipolytica* or *Schizosaccharomyces pombe* are particularly suitable as the yeast host. Suitable vectors are known to a person skilled in the art such as pPICZαA, pIIC9K, Yes vectors, pTEF1/Zeo, pYDI (e.g. Invitrogen). The expression vector that is formed in this manner is preferably transformed into various strains of *Pichia pastoris* and integrated into the genome in a stable manner. Stable integration into the yeast genome has the advantage that selection pressure is not required during the subsequent production of the, for example, eukaryotic, highly active alkaline phosphatase in large volume ferments. Stable integration into the genome means that the expression vector is incorporated into the genome of for example *Pichia pastoris* by means of homologous recombination and is thus transmitted by heredity as a permanent component from generation to generation (Cregg, J. M. et al., Mol. Cell. Biol. 5 (1985), 3376–3385).

The gene copy number was increased in the methylotrophic yeast by multiple transformation while at the same time increasing the selection pressure with a suitable selection marker e.g. an antibiotic such as Zeocin® or Geneticin (G418) or an auxotrophy marker after which only those clones can survive which have integrated several copies of the expression vector into the genome in a stable manner. In order to be resistant to higher concentrations of the antibiotic used as the selection marker, it is necessary that the clones produce an increasing amount of resistance protein. This can for example be achieved by multiple integration of the expression vector which contains the resistance gene for the antibiotic used as the selection marker in addition to the expression cassette for the highly active alkaline phosphatase for example.

The object of producing eukaryotic alkaline phosphatase economically in a robust and stable expression process with a high expression output could not be achieved until measures (i) to (vi) were combined. Thus for example transformation of a Pichia pastoris strain X-33 with an expression vector which contains the bIAPII gene according to SEQ ID NO: 1 did not lead to the desired result without these measures (see examples 1 and 2). Although the process enabled a considerable increase in the expression output compared to expression of bIAPII in CHO cells (Manes et al., 1998, J. Biol. Chem. 273 No.36, 23353–23360) the process does not allow a recombinant alkaline phosphatase to be produced economically.

One of the necessary measures for the process according to the invention is the synthesis of a codon-optimized gene sequence. A complete de novo synthesis of the ca. 1,5 kBp long gene which codes for the eukaryotic highly active alkaline phosphatase was necessary in order to optimize each codon for expression in yeast. It was possible to optimize each codon, as required, by retranslation of the amino acid sequence of the eukaryotic highly active alkaline phosphatase according to SEQ ID NO: 4 (bIAP-II) and by utilizing the degenerate code. For this purpose the gene was divided into 28 oligonucleotides having a length of 54 to 82 nucleotides. The oligonucleotides were designed as an alternating sequence of sense strand and antistrand fragments the 5' and 3' ends of which each overlapped in a complementary manner with the neighbouring oligonucleotides. The overlapping region was in each case selected in such a manner that unspecific binding was largely prevented during the annealing reaction in the subsequent PCR reaction. The oligonucleotides at the 5' and 3' ends of the gene were provided with recognition sites for restriction endonucleases upstream and downstream of the coding region which could be used for a later insertion of the synthetic gene according to SEQ ID NO: 5 into expression vectors. Hence a recognition site for the restriction endonuclease EcoRI was incorporated upstream and a recognition site for the restriction endonuclease Asp718 was incorporated downstream. The sequences of the oligonucleotides are shown in SEQ ID NO: 6 to 33.

The gene synthesis was carried out by means of a PCR reaction. For this purpose the coding region was firstly divided into three segments (oligonucleotides 6 to 15, 16 to 23, 24 to 33) and these segments were generated in separate PCR reactions. During the gene synthesis by means of PCR reaction using overlapping complementary oligonucleotides the gene fragment is elongated stepwise to form the full length product which is then amplified in subsequent cycles. The annealing temperature in this process depends on the overlapping region having the lowest melting temperature.

The three segments were subsequently analysed by agarose gel electrophoresis, the products having the expected length were isolated from the gel by means of the QIAquick gel extraction kit (Qiagen) and synthesized in a further PCR reaction to form the complete gene product. In this process the PCR reaction was carried out in the first 5 cycles without adding the primers at the 5' end and at the 3' end of the total gene so that only a few fragments of the gene product having the expected length were initially formed from the three segments. The annealing temperature depends on the overlapping region having the lowest melting temperature. Subsequently the terminal primers were added and the annealing temperature was increased to correspond with the annealing temperature of the primer having the lowest melting temperature. The gene fragment having the expected length was amplified to a high degree in a further 25 cycles.

The PCR mixture was analysed by agarose gel electrophoresis and the gene fragment having the expected size was isolated (QIAquick gel extraction kit/Qiagen).

The cloning of such a PCR fragment, transformation in *Pichia pastoris* and the expression is described in example 3.

The codon-optimized gene for the highly active alkaline phosphatase enabled the expression output to be increased three-fold compared to the first experiments with the wild-type gene.

However, these clones did not provide an economic process for producing the highly active alkaline phosphatase.

One measure which can increase the expression output of heterologous and homologous proteins in *Pichia pastoris* is to increase the gene copy number in the cell by multiple transformation. This measure can increase the transcription product i.e. the mRNA of the target gene. The gene copy number is increased by multiple transformation of a clone containing the expression vector while simultaneously increasing the selection pressure during the subsequent growth of the transformants on nutrient plates containing increased concentrations of the antibiotic used as the selection marker. In this process an expression clone which has already taken up at least one copy of the expression vector from the first transformation cycle is again made competent (see example 1) and is again transformed with the expression vector. Transformants are selected which have integrated several copies of the expression vector into the genome by plating out on nutrient plates with a higher selection pressure i.e. plates containing a higher concentration of the antibiotic (e.g. Zeocin®) used as the selection marker than during the first transformation cycle. For this the highest concentration of the antibiotic used as the selection marker at which the clone from the first transformation cycle can still grow is determined and the concentration of the antibiotic used as the selection marker is increased accordingly above the determined threshold value in the YPDS agar plates after the additional transformation. Increasing the copy number of the expression vector also increases the copy number of the resistance gene which is a component of the expression vector and hence also increases resistance to higher concentrations of the antibiotic used as the selection marker. It is also possible to select clones containing different copy numbers of the expression vector in the genome by varying the concentration of the antibiotic used as the selection marker in the nutrient plates (ca. 100 to 2000 µg/ml/see example 4).

A further measure which can be used to increase the expression output of heterologous and homologous proteins in yeast such as *Pichia pastoris* is to increase the gene copy number by multiple selection. In order to achieve this an expression clone that has been already optimized by multiple transformation with an expression vector which contains the expression cassette containing the target gene (e.g. the gene which codes for the highly active alkaline phosphatase according to SEQ ID NO: 5) and a resistance gene for the first antibiotic used as the selection marker (e.g. Zeocin®) is transformed with a second expression vector which contains the target gene (e.g. the gene which codes for the highly active alkaline phosphatase according to SEQ ID NO: 5) and a resistance gene for the second antibiotic (e.g. Geneticin (G418)) used as the selection marker. When the transformants are subsequently plated out on nutrient plates which contain the second antibiotic as the selection marker, only those clones are selected which have also taken up at least one copy of the expression vector containing the resistance gene for the second antibiotic used as the selection marker in addition to copies of the expression vector containing the resistance gene for the first antibiotic used as the selection marker. These expression clones can now be in turn subjected to a further multiple transformation with the expression vector containing the resistance gene for the second antibiotic used as the selection marker (see example 5).

By combining the measures of multiple transformation and double selection it was possible to increase the expression output four-fold compared to the expression output of clones from the first transformation cycle containing the codon-optimized gene.

The recombinant alkaline phosphatase can be extracted from the biomass by extraction methods that are in principle known to a person skilled in the art e.g. Protein Purification, Springer Verlag, editor Robert Scopes (1982). A pure band product having a specific activity of more than 7000 U/mg is obtained by chromatographic separation methods and especially those using hydrophobic column materials and a cation exchanger.

The purified product was subjected to N-terminal sequencing in order to characterize the recombinant highly active alkaline phosphatase.

The dominant sequence EAEAEFLIPA (SEQ ID NO: 36) was determined. The sequence unequivocally correlates with the N-terminal sequence of the AP"LIPA" (SEQ ID NO: 37) and with the linker peptide of the construct EAE-AEF (SEQ ID NO: 38) which is formed by the strategy of cloning the gene sequence into the vector and by cleavage of the α-factor signal peptide by a Kex2 signal peptidase (e.g. Invitrogen).

The stability of the recombinant alkaline phosphatase product was examined in comparison with the naturally occurring alkaline phosphatase. The samples yielded comparable results when the solutions were subjected to a thermal stress (55° C.).

Hence the present invention describes for the first time a process which enables an economic production of a recombinant alkaline phosphatase from mammalian cells such as bovine intestine which has properties that are comparable to the native highly active alkaline phosphatase from bovine intestine and is glycosylated.

The present invention also concerns a DNA sequence according to SEQ ID NO: 5 as a codon-optimized gene sequence for the expression of the gene for the highly active alkaline phosphatase in *Pichia pastoris*.

Figure 2:
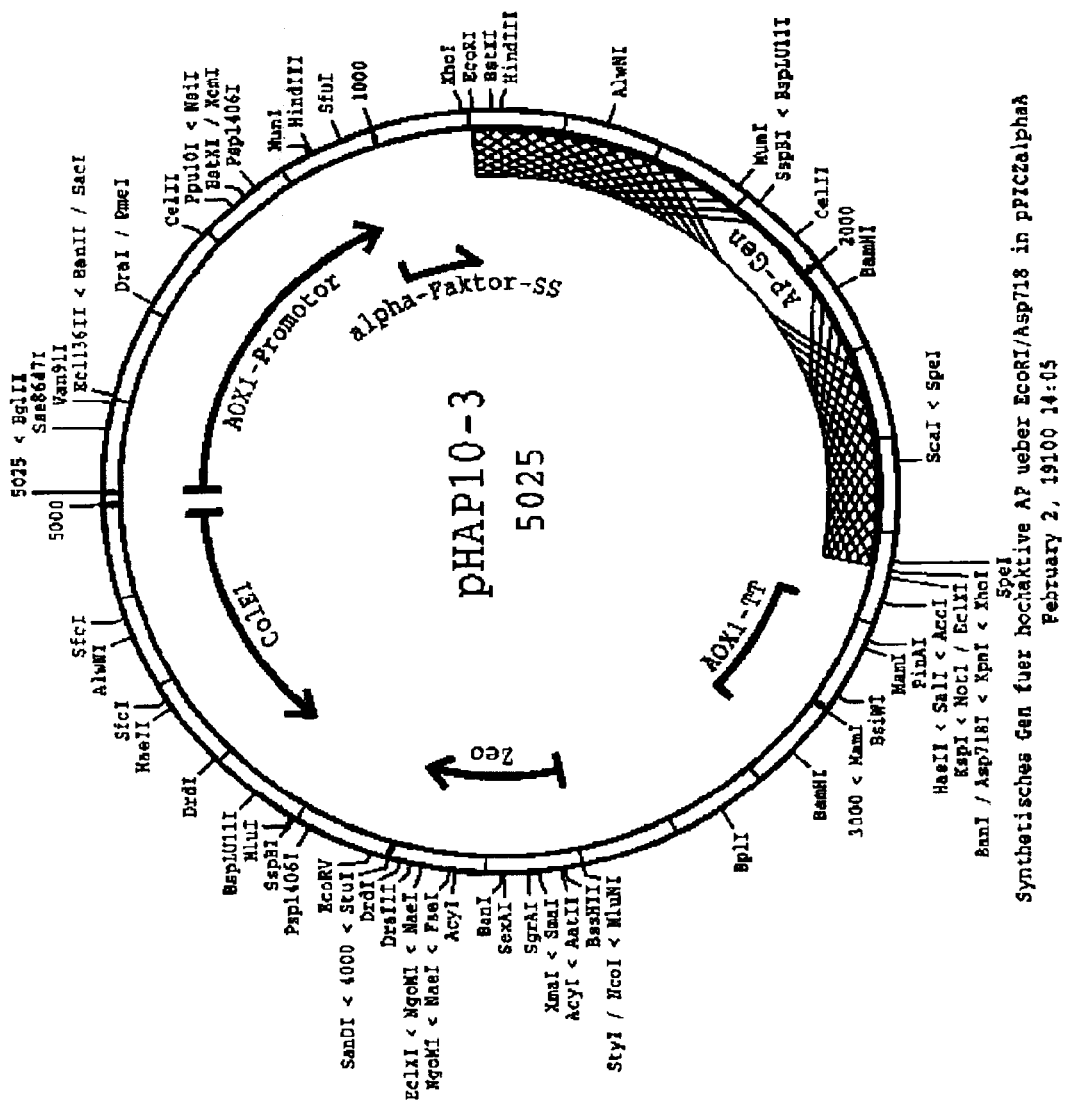

A further subject matter of the invention is a vector containing SEQ ID NO: 5 and particularly preferably the vector pHAP10-3 according to FIG. 2. pHAP10-3 is the vector pPICZαA which is commercially available (Invitrogen) and contains the inventive gene according to SEQ ID NO: 5 which is under the control of the AOX 1 promoter.

A further subject matter of the invention is a host strain which has been transformed with the vectors according to the invention. The *Pichia pastoris* X-33 strain transformed with the vector pHAP10-3 is particularly preferred.

Figure 3:
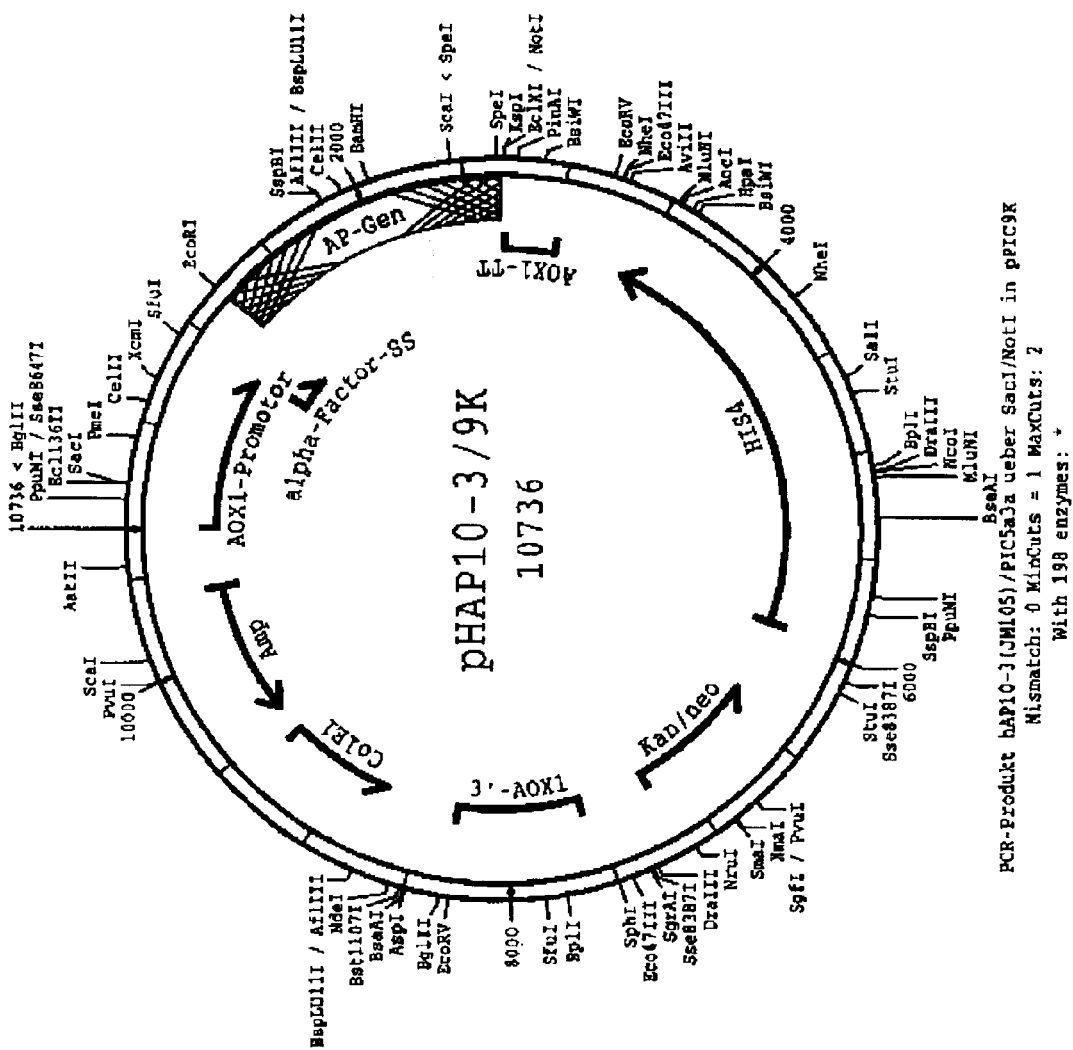

Another preferred vector is a vector which contains the entire expression cassette from pHAP10-3 which essentially comprises the AOX 1 promoter, the signal peptide of the α-factor from *Saccharomyces cerevisiae* which is cloned in the correct reading frame behind the signal peptide, the codon-optimized target gene according to SEQ ID NO: 5 which codes for the highly active alkaline phosphatase and the AOX 1 transcription termination region (see fig.3). The vector pHAP 10-3/9K is particularly preferred which comprises the commercially available vector pPIC9K (Invitrogen) and the expression cassette from pHAP 10-3 including the synthetic gene according to SEQ ID NO: 5.

The vectors pHAP 10- 3 and pHAP 10-3/9K are equally relevant since the final production clone contains copies of both vectors.

A further subject matter of the invention is a host strain which has been transformed with the pHAP10-3/9K vector. However, other vectors and strains known to a person skilled in the art are also suitable in the sense of the present invention such as YES vectors, pYD1, pTEF 1/ZEO (Invitrogen) and *Saccharomyces cerevisiae*, Schizosaccharomyces pombe, Hansenula polymorpha, Yarrowia lipolytica and in particular *Pichia pastoris* X-33. The *Pichia pastoris* X-33 strain transformed with the vector pHAP10-3/9K is especially preferable for the invention.

Hence a further subject matter of the invention is a process for producing a eukaryotic highly active alkaline phosphatase by expressing the protein in a host strain which has been transformed with one or several vectors according to the invention and especially with the pHAP 10-3 vector or the pHAP 10-3/9K vector. *Pichia pastoris* strains which have been transformed with the inventive vectors are particularly preferred for the inventive process. The strain *Pichia pastoris* X-33 which has been transformed with a pHAP 10-3 and a pHAP 10-3/9K vector is especially preferred in this connection.

FIGURES

FIG. 1

Plasmid map of the expression vector pHAP-1 containing the bIAPII gene in pICZαA (Invitrogen).

FIG. 2

Plasmid map of the expression vector pHAP 10-3 containing the synthetic gene in pPIC9K (Invitrogen).

FIG. 3

Plasmid map of the expression vector pHAP 10-3/9K containing the synthetic gene in pPIC9K (Invitrogen).

Abbreviations

| | |
|---|---|
| YPD: | yeast peptone dextrose |
| YPDS: | yeast peptone dextrose sorbitol |
| BMGY: | buffered glycerol complex medium |
| BMMY: | buffered methanol complex medium |

EXAMPLE 1

Cloning the bIAPII Gene

The bIAPII gene according to SEQ ID NO: 1 (EP 0 955 369; Manes et al., 1998, *J. Biol. Chem.* 273 No. 36, 23353–23360) was firstly provided upstream and downstream with restriction endonuclease cleavage sites suitable for cloning into expression vectors for *Pichia pastoris* by means of PCR and selection of suitable primers according to SEQ ID NO: 2 and 3. Hence the restriction endonuclease cleavage site for EcoRI was attached upstream and the restriction endonuclease cleavage site for Asp718 I was attached downstream.

The PCR fragment was recleaved with EcoRI and Asp718 I (Roche Diagnostics GmbH), isolated again (QIAquick gel extraction kit/Qiagen) and subsequently ligated into a vector fragment of the expression vector pPICZαA (Invitrogen) that had been linearized with EcoRI and Asp718 I (Roche Diagnostics GmbH) and isolated (QIAquick gel extraction kit/Qiagen). In this vector the bIAPII gene is under the control of the AOX 1 promoter (promoter for alcohol oxidase 1 from *Pichia pastoris* and inducible with methanol) and is cloned in the correct reading frame behind the signal peptide of the α-factor from *Saccharomyces cerevisiae*. It was then examined whether the gene fragment inserted in this manner was free of errors by means of restriction analysis and sequencing. The expression vector formed in this manner which contains the bIAPII gene which codes for the eukaryotic highly active alkaline phosphatase was named pHAP-1 (see FIG. 1).

Transformation of pHAP-1 in *Pichia pastoris*

For the transformation of pHAP-1 in *Pichia pastoris* X-33 and subsequent integration into the genome, the vector was firstly linearized with SacI (Roche Diagnostics GmbH). The transformation was carried out by means of electroporation using a Gene Pulser II (Biorad).

For this 5 ml YPD medium (Invitrogen) was inoculated with a colony of Pichia pastoris wild-type strain and incubated at 30° C. overnight while shaking. 200 ml fresh YPD medium (Invitrogen) was subsequently transfer inoculated 1:2000 with the overnight culture and incubated overnight at 30° C. while shaking until the $OD_{600}$ reached 1.3 –1.5. The cells were centrifuged (1500×g/5 minutes) and the pellet was resuspended in 200 ml ice-cold sterile water (0° C.). The cells were again centrifuged (1500×g/5 minutes) and resuspended in 100 ml ice-cold, sterile water (0° C.). The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells obtained in this manner were kept on ice and used immediately for transformation.

Ca. 1 μg linearized pHAP-1 vector DNA was added to 80 μl of the cells and the entire mixture was transferred to an ice-cold (0° C.) electroporation cuvette and incubated for a further 5 minutes on ice. Subsequently the cuvette was transferred to the Gene Pulser II (Biorad) and the transformation was carried out at 1 kV, 1 kΩ and 25 μF. After electroporation, 1 ml 1 M sorbitol (ICN) was added to the mixture and subsequently 100 to 150 μl was plated out on a YPDS agar plate (Invitrogen) containing 100 μg/ml Zeocin® (Invitrogen). The plates were subsequently incubated at 30° C. for 2–4 days.

Raster MD (=minimal dextrose) plates were inoculated with the clones and they were analysed further. Growing clones were picked out, resuspended in 20 μl sterile water, lysed with 17.5 U lyticase (Roche Diagnostics GmbH) (1 hour, 37° C.) and examined directly for the correct integration of the bIAPII expression cassette by means of PCR.

Clones which had integrated the complete expression cassette during transformation into the genome were then used in expression experiments.

Expression of the Highly Active Alkaline Phosphatase 3 ml BMGY medium (Invitrogen) was inoculated with positive clones and incubated overnight at 30° C. while shaking. Subsequently the OD was determined at 600 nm and 10 ml BMMY medium (Invitrogen) was transfer inoculated in such a manner that an $OD_{600}$ of 1 was obtained. The BMMY medium (Invitrogen) contains methanol (Mallinckrodt Baker B. V.) which induces the expression of the highly active alkaline phosphatase via the AOX 1 promoter.

The shaking flasks were incubated at 30° C. while shaking, samples were taken every 24 hours, the $OD_{600}$ was determined, an activity test for the expression of the highly active alkaline phosphatase was carried out and 0.5 % methanol (Mallinckrodt Baker B. V.) was added for the further induction. The expression experiments were carried out for 96 hours.

EXAMPLE 2

Activity Test for the Highly Active Alkaline Phosphatase

500 μl of the expression culture of example 1 was removed, the $OD_{600}$ was determined and the cells were centrifuged. The supernatant was stored and the cell pellet was resuspended for the lysis in an amount of Y-PER™ (50 to 300 μl/Pierce) corresponding to the $OD_{600}$ and shaken for 1 hour at room temperature. Subsequently the lysate was centrifuged to remove cell debris (15000×g/5 minutes) and the supernatant was transferred to fresh reaction vessels. 5 μl of the lysate was then used in the activity test.

The principle of the activity test is as follows:

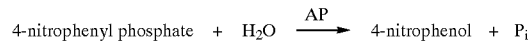

The increase in absorbance at 405 nm is measured.

50 μl 4-nitrophenyl phosphate solution (0.67 mol/l 4-nitrophenyl phosphate, Na salt (Roche Diagnostics GmbH)) was added to 3 ml diethanolamine buffer (1 mol/l diethanolamine (Merck) pH 9.8, 0.5 mmol/l $MgCl_2$ (Riedel de Haen)) and the mixture was incubated at 37° C. Subsequently the reaction was started by adding 5 μl lysate and the change in absorbance at 37° C. was determined for 3 minutes and from this the ΔA/min was calculated.

The activity was then calculated according to the following formula:

$$\text{activity} = \frac{3.10}{\varepsilon \times 0.005 \text{ x1}} \times \Delta A / \text{min} \times \frac{1}{\text{factor } x} [\text{U/ml sample solution}]$$

$\varepsilon = 18.2 \ [1 \times \text{mmol}^{-1} \times \text{cm}^{-1}]$ factor *x*=concentration factor after cell lysis The activity of the medium supernatant of the expression cultures was determined in a similar manner. The reaction in this case was also started with 5 µl of the supernatant but 0.5 mM ZnCl$_2$ was added additionally. In this case the calculation was carried out without factor x.

EXAMPLE 3

Cloning the PCR Fragment from the Gene Synthesis

The PCR fragment was recleaved with EcoRI and Asp718 (Roche Diagnostics GmbH), isolated again (QIAquick gel extraction kit/Qiagen) and subsequently ligated into a vector fragment of the expression vector pPICZαA (Invitrogen) that had been linearized with EcoRI and Asp718 (Roche Diagnostics GmbH) and isolated (QIAquick gel extraction kit/Qiagen). In this vector the synthetic gene is under the control of the AOX 1 promoter (promoter for alcohol oxidase 1 from *Pichia pastoris*, inducible with methanol (Mallinckrodt Baker B. V.) and is cloned in the correct reading frame behind the signal peptide of the α-factor from *Saccharomyces cerevisiae*. It was then examined whether the gene fragment inserted in this manner was free of errors by means of restriction analysis and sequencing. The expression vector formed in this manner which contains a synthetic gene which codes for the eukaryotic highly active alkaline phosphatase was named pHAP10-3 (see FIG. 2).

Transformation of pHAP10-3 in *Pichia pastoris*

For the transformation of pHAP10-3 in *Pichia pastoris* X-33 and subsequent integration into the genome, the vector was firstly linearized with SacI (Roche Diagnostics GmbH). The transformation was carried out by means of electroporation using a Gene Pulser II (Biorad). For this 5 ml YPD medium (Invitrogen) was inoculated with a colony of *Pichia pastoris* and incubated at 30° C. overnight while shaking. 200 ml fresh YPD medium (Invitrogen) was subsequently transfer inoculated 1:2000 with the overnight culture and incubated overnight at 30° C. while shaking until the OD$_{600}$ reached 1.3–1.5. The cells were centrifuged (1500×g/5 minutes) and the pellet was resuspended in 200 ml ice-cold sterile water (0° C.). The cells were again centrifuged (1500×g/5 minutes) and resuspended in 100 ml ice-cold, sterile water (0° C.). The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells obtained in this manner were kept on ice and used immediately for transformation.

Ca. 1 µg linearized pHAP10-3 vector DNA was added to 80 µl of the cells and the entire mixture was transferred to an ice-cold (0° C.) electroporation cuvette and incubated for a further 5 minutes on ice. Subsequently the cuvette was transferred to the Gene Pulser II (Biorad) and the transformation was carried out at 1 kV, 1 kΩ and 25 µF. After electroporation 1 ml 1 M sorbitol (ICN) was added to the mixture and subsequently 100 to 150 µl was plated out on a YPDS agar plate (Invitrogen) containing 100 µg/ml Zeocin® (Invitrogen). The plates were subsequently incubated at 30° C. for 2–4 days.

Raster MD (=minimal dextrose) plates were inoculated with the clones and they were analysed further. Growing clones were picked out, resuspended in 20 µl sterile water, lysed with 17.5 U lyticase (Roche Diagnostics GmbH) (1 hour, 37° C.) and examined directly for the correct integration of the synthetic AP expression cassette by means of PCR.

Clones which had integrated the complete expression cassette during transformation into the genome were then used in expression experiments.

Expression of the Highly Active Alkaline Phosphatase 3 ml BMGY medium (Invitrogen) was inoculated with positive clones and incubated overnight at 30° C. while shaking. Subsequently the OD was determined at 600 nm and 10 ml BMMY medium (Invitrogen) was transfer inoculated in such a manner that an OD$_{600}$ of 1 was obtained. The BMMY medium (Invitrogen) contains methanol (Mallinckrodt Baker B. V.) which induces the expression of the highly active alkaline phosphatase via the AOX 1 promoter.

The shaking flasks were incubated at 30° C. while shaking, samples were taken every 24 hours, the OD$_{600}$ was determined, an activity test for the expression of the highly active alkaline phosphatase was carried out and 0.5% methanol (Mallinckrodt Baker B. V.) was added for the further induction. The expression experiments were carried out for 96 hours.

Activity Test for the Highly Active Alkaline Phosphatase

500 µl of the expression culture was removed, the OD$_{600}$ was determined and the cells were centrifuged. The supernatant was stored and the cell pellet was resuspended for lysis in an amount of Y-PER™ (50 to 300 µl/Pierce) corresponding to the OD$_{600}$ and shaken for 1 hour at room temperature. Subsequently the lysate was centrifuged to remove cell debris (15000×g/5 minutes) and the supernatant was transferred to fresh reaction vessels. 5 µl of the lysate was then used in the activity test.

The activity test was carried out as described above.

EXAMPLE 4

Increasing the Expression Output by Multiple Transformation

The best clones from the expression experiments were in turn prepared for extrapolation as described above and again transformed with 1 µg linearized pHAP10-3 vector DNA and the transformation mixture was plated out on YPDS agar plates (Invitrogen) containing 1000 to 2000 µg/ml Zeocin® (Invitrogen). As a result the selection pressure was increased to such an extent that only clones could grow that had integrated several copies of the expression vector pHAP10-3 and thus also several copies of the respective resistance gene (in this case Zeocin®) into the genome. The Zeocin® resistance protein is the product of the bleomycin gene of *Streptoalloteichus hindustanus* (Chalmels, T. et al., Curr. Genet. 20 (1991), 309–314; Drocourt, D. et al., Nucleic Acid Research 18 (1990), 4009) which binds Zeocin® in a stoichiometric concentration ratio and thus makes the cell resistant to Zeocin®. The higher the concentration of Zeocin® in the YPDS agar plates, the more resistance protein the cell has to generate in order to quantitatively bind the Zeocin® and thus enable growth. This is possible for example when multiple copies of the resistance gene have been integrated into the genome. As described above raster MD plates were transfer inoculated with the clones and they were again checked as described above by PCR analysis for the correct integration of the haAP expression cassette. Subsequently these clones were in turn tested for haAP activity as described above.

EXAMPLE 5

Increasing the Expression Output by Using a Second Selection Pressure

Increasing the Zeocin® concentration above 2000 µg/ml did not lead to an improvement in the expression output of the highly active alkaline phosphatase. In order to further increase the gene copy number in the expression clones of the gene according to SEQ ID NO: 5 which codes for the highly active alkaline phosphatase and which is codon-optimized for expression in yeast, the integration of additional expression vectors into the genome of the expression clone derived from examples 3 and 4 that had the highest expression output was selected by means of a second selection pressure, preferably G418 (Roche Diagnostics GmbH). For this purpose the entire expression cassette from pHAP10-3 comprising AOX1 promoter, signal peptide of the α-factor from *Saccharomyces cerevisiae*, codon-optimized gene for the highly active alkaline phosphatase according to SEQ ID NO: 5 and AOX 1 transcription termination region isolated by means of PCR using appropriately selected primers as described below, was cloned into the vector pIC9K the integration of which into the genome of *Pichia pastoris* was selected by means of G418 (Roche Diagnostics GmbH). The primers are shown in SEQ ID NO: 34 and 35.

The PCR mixture was analysed by agarose gel electrophosis, the gene fragment having the expected size was isolated (QIAquick gel extraction kit/Qiagen), recleaved with SaCI and NotI (Roche Diagnostics GmbH), subsequently isolated again from the agarose gel (QIAquick gel extraction kit/Qiagen) and ligated into an isolated vector fragment from pIC9K that had also been linearized with SacI/NotI (Roche Diagnostics GmbH). This ensures that the entire expression cassette from pHAP10-3 is present in an identical form in pPIC9K. The inserted fragment was checked by means of restriction analysis and sequencing with the flanking regions. The expression vector formed in this manner was named pHAP10-3/9K (see FIG. 3).

The clones with the highest haAp expression output from the multiple transformation with pHAP10-3 (Zeocin resistance) were prepared for electroporation as described above and transformed as described above with 1 μg of the vector fragment from pHAP10-3/9K linearized with SacI (Roche Diagnostics GmbH). The transformation mixture was subsequently stored for 1 to 3 days at 4° C. in 1 M sorbitol (ICN) (to form the G418 resistance) and 100 to 200 μl was plated out on YPD plates (Invitrogen) containing 1, 2 and 4 mg/ml G418 (Roche Diagnostics GmbH) and incubated for 3 to 5 days at 30° C. The resulting clones were again examined by means of the activity test for an increased expression of the eukaryotic highly active alkaline phosphatase as described above.

What is claimed is:

1. A DNA sequence comprising the sequence of SEQ ID NO: 5.

2. A transformation vector comprising the sequence of SEQ ID NO: 5.

3. A process for selecting yeast transformants useful in the production of a eukaryotic alkaline phosphatase, said process comprising the steps of:
  (a) transforming yeast cells with a vector comprising a first marker gene encoding resistance to a first antibiotic and an alkaline phosphatase coding sequence selected from the group consisting of SEQ ID NO: 1 and SEQ ID NO: 5;
  (b) selecting transformants that grow in medium containing a first concentration of the first antibiotic;
  (c) further transforming the selected transformants with a vector comprising the first marker and the alkaline phosphatase coding sequence;
  (d) identifying transformants that have incorporated multiple copies of the alkaline phosphatase coding sequence by selecting those transformants that grow in medium containing a second concentration of the first antibiotic, said second concentration being higher than the first concentration;
  (e) further transforming the identified transformants with a vector comprising a second marker gene encoding resistance to a second antibiotic and the alkaline phosphatase coding sequence; and
  (f) selecting transformants that grow in medium containing the second antibiotic.

4. The process as claimed in claim 3, wherein the yeast cells are methylotrophic.

5. The process as claimed in claim 3, wherein the yeast cells are *Pichia pastoris* or *Hansenula polymorpha*.

6. The process as claimed in claim 3, wherein the transformants that grow in medium containing the second antibiotic are transformed at least once more with a vector comprising the second marker gene and the alkaline phosphatase coding sequence and the transformants that grow in medium containing the second antibiotic are selected.

7. A process for the production of a eukaryotic alkaline phosphatase in yeast cells comprising the steps of selecting a transformant according to the process of claim 3, expressing the alkaline phosphatase, and purifying the alkaline phosphatase.

* * * * *

SEQUENCE LISTING

<160> NUMBER OF SEQ ID NOS: 38

<210> SEQ ID NO 1
<211> LENGTH: 1476
<212> TYPE: DNA
<213> ORGANISM: Bovine

<400> SEQUENCE: 1

```
gaattcctca tcccagctga ggaggaaaac cccgccttct ggaaccgcca ggcagcccag      60
gcccttgatg tagccaagaa gttgcagccg atccagacag ctgccaagaa tgtcatcctc     120
ttcttggggg atgggatggg ggtgcctacg gtgacagcca ctcggatcct aaagggcag     180 atgaatggca aactgggacc tgagacaccc ctggccatgg accagttccc atacgtggct     240
ctgtccaaga catacaacgt ggacagacag gtgccagaca gcgcaggcac tgccactgcc     300
tacctgtgtg gggtcaaggg caactacaga accatcggtg taagtgcagc cgcccgctac     360
aatcagtgca acacgacacg tgggaatgag gtcacgtctg tgatcaaccg ggccaagaaa     420
gcagggaagg ccgtgggagt ggtgaccacc accagggtgc agcatgcctc cccagccggg     480
gcctacgcgc acacggtgaa ccgaaactgg tactcagacg ccgacctgcc tgctgatgca     540
cagaagaatg gctgccagga catcgccgca cagctggtct acaacatgga tattgacgtg     600
atcctgggtg gaggccgaat gtacatgttt cctgagggga ccccagaccc tgaatacca     660 gatgatgcca gtgtgaatgg agtccggaag gacaagcaga acctggtgca ggaatggcag     720
gccaagcacc agggagccca gtatgtgtgg aaccgcactg cgctccttca ggcggccgat     780
gactccagtg taacacacct catgggcctc tttgagccgg cagacatgaa gtataatgtt     840
cagcaagacc acaccaagga cccgaccctg gcggagatga cggaggcggc cctgcaagtg     900
ctgagcagga accccgggg cttctacctc ttcgtggagg gaggccgcat tgaccacggt     960
caccatgacg gcaaagctta tatggcactg actgaggcga tcatgtttga caatgccatc    1020
gccaaggcta acgagctcac tagcgaactg gacacgctga tccttgtcac tgcagaccac    1080
tcccatgtct tctcttttgg tggctacaca ctgcgtggga cctccatttt cggtctggcc    1140
cccggcaagg ccttagacag caagtcctac acctccatcc tctatggcaa tgcccaggc    1200 tatgcgcttg gcggggctc gaggcccgat gttaatggca gcacaagcga ggaaccctca    1260
```

-continued

```
taccggcagc aggcggccgt gcccctggct agcgagaccc acgggggcga agacgtggcg    1320
gtgttcgcgc gaggcccgca ggcgcacctg gtgcacggcg tgcaggagga gaccttcgtg    1380
gcgcacatca tggcctttgc gggctgcgtg gagccctaca ccgactgcaa tctgccagcc    1440
cccgccaccg ccaccagcat ccccgactag ggtacc                              1476
```

<210> SEQ ID NO 2
<211> LENGTH: 40
<212> TYPE: DNA
<213> ORGANISM: Artificial Sequence
<220> FEATURE:
<223> OTHER INFORMATION: Primer

<400> SEQUENCE: 2

```
gcgcgaattc ctcatcccag ctgaggagga aaaccccgcc                          40
```

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3

```
cgcgggtacc ctagtcgggg atgctggtgg cggtgg                              36
```

<210> SEQ ID NO 4
<211> LENGTH: 487
<212> TYPE: PRT
<213> ORGANISM: Bovine

<400> SEQUENCE: 4

```
Leu Ile Pro Ala Glu Glu Asn Pro Ala Phe Trp Asn Arg Gln Ala
1               5                   10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
    50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205
```

```
Pro Glu Gly Thr Pro Asp Pro Glu Tyr Pro Asp Ala Ser Val Asn
    210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
        275                 280                 285

Ala Glu Met Thr Glu Ala Ala Leu Gln Val Leu Ser Arg Asn Pro Arg
    290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
        355                 360                 365

Leu Arg Gly Thr Ser Ile Phe Gly Leu Ala Pro Gly Lys Ala Leu Asp
    370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
        435                 440                 445

Val His Gly Val Gln Glu Glu Thr Phe Val Ala His Ile Met Ala Phe
    450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 5
<211> LENGTH: 1476
<212> TYPE: DNA
<213> ORGANISM: Artificial Sequence
<220> FEATURE:
<223> OTHER INFORMATION: Codon-optimized DNA sequence

<400> SEQUENCE: 5
gaattcttga ttccagctga agaagaaaat ccagcttttt ggaatagaca agctgctcaa    60
gctttggatg ttgctaagaa gttgcaacca attcaaactg ctgctaagaa tgttattttg   120
tttttgggtg atggtatggg tgttccaact gttactgcta ctagaatttt gaagggtcaa   180
atgaatggta gttgggtcc agaaactcca ttggctatgg atcaatttcc atacgttgct   240
ttgtctaaga cttacaatgt tgatagacaa gttccagatt ctgctggtac tgctactgct   300
tacttgtgtg gtgttaaggg taattacaga actattggtg tttctgctgc tgctagatac   360
aatcaatgta atactactag aggtaatgaa gttacttctg ttattaatag agctaagaag   420
```

```
gctggtaagg ctgttggtgt tgttactact actagagttc aacatgcttc tccagctggt    480
gcttacgctc atactgttaa tagaaattgg tactctgatg ctgatttgcc agctgatgct    540
caaaagaatg gttgtcaaga tattgctgct caattggttt acaatatgga tattgatgtt    600
attttgggtg gtggtagaat gtacatgttt ccagaaggta ctccagatcc agaataccca    660
gatgatgctt ctgttaatgg tgttagaaag gataagcaaa atttggttca agaatggcaa    720
gctaagcatc aaggtgctca atatgttggg aatagaactg ctttgttgca agctgctgat    780
gattctagtg ttactcattt gatgggtttg tttgaaccag ctgatatgaa gtataatgtt    840
caacaagatc atactaagga tccaactttg gctgaaatga ctgaagctgc tttgcaagtt    900
ttgtctagaa atccaagagg ttttttacttg tttgttgaag gtggtagaat tgatcatggt    960
catcatgatg gtaaggctta tatggctttg actgaagcta ttatgtttga taatgctatt   1020
gctaaggcta atgaattgac ttctgaattg atactttga ttttggttac tgctgatcat    1080
agtcatgttt tttctttggg tggttacact ttgagaggta cttctatttt tggtttggct   1140
ccaggtaagg ctttggatag taagtcttac acttctatttt tgtatggtaa tggtccaggt   1200
tatgctttgg gtggtggttc tagaccagat gttaatggta gtactagtga agaaccatct   1260
tacagacaac aagctgctgt tccattggct agtgaaactc atggtggtga agatgttgct   1320 gttttttgcta gaggtccaca agctcatttg gttcatggtg ttcaagaaga aactttttgtt   1380 gctcatatta tggcttttgc tggttgtgtt gaaccataca ctgattgtaa tttgccagct   1440
ccagctactg ctactagtat tccagattaa ggtacc                             1476
```

```
<210> SEQ ID NO 6
<211> LENGTH: 78
<212> TYPE: DNA
<213> ORGANISM: Artificial Sequence
<220> FEATURE:
<223> OTHER INFORMATION: Primer

<400> SEQUENCE: 6
gcgcgaattc ttgattccag ctgaagaaga aaatccagct ttttggaata gacaagctgc    60
tcaagctttg gatgttgc                                                  78

<210> SEQ ID NO 7
<211> LENGTH: 70
<212> TYPE: DNA
<213> ORGANISM: Artificial Sequence
<220> FEATURE:
<223> OTHER INFORMATION: Primer

<400> SEQUENCE: 7
ccaaaaacaa aataacattc ttagcagcag tttgaattgg ttgcaacttc ttagcaacat    60
ccaaagcttg                                                           70

<210> SEQ ID NO 8
<211> LENGTH: 69
<212> TYPE: DNA
<213> ORGANISM: Artificial Sequence
<220> FEATURE:
<223> OTHER INFORMATION: Primer

<400> SEQUENCE: 8
gaatgttatt ttgttttttgg gtgatggtat gggtgttcca actgttactg ctactagaat    60
tttgaaggg                                                            69
```

<210> SEQ ID NO 9
<211> LENGTH: 70
<212> TYPE: DNA
<213> ORGANISM: Artificial Sequence
<220> FEATURE:
<223> OTHER INFORMATION: Primer

<400> SEQUENCE: 9
ggaaattgat ccatagccaa tggagtttct ggacccaact taccattcat ttgacccttc    60
aaaattctag                                                          70

<210> SEQ ID NO 10
<211> LENGTH: 71
<212> TYPE: DNA
<213> ORGANISM: Artificial Sequence
<220> FEATURE:
<223> OTHER INFORMATION: Primer

<400> SEQUENCE: 10
gctatggatc aatttccata cgttgctttg tctaagactt acaatgttga tagacaagtt    60
ccagattctg c                                                        71

<210> SEQ ID NO 11
<211> LENGTH: 71
<212> TYPE: DNA
<213> ORGANISM: Artificial Sequence
<220> FEATURE:
<223> OTHER INFORMATION: Primer

<400> SEQUENCE: 11
ccaatagttc tgtaattacc cttaacacca cacaagtaag cagtagcagt accagcagaa    60
tctggaactt g                                                        71

<210> SEQ ID NO 12
<211> LENGTH: 72
<212> TYPE: DNA
<213> ORGANISM: Artificial Sequence
<220> FEATURE:
<223> OTHER INFORMATION: Primer

<400> SEQUENCE: 12
gtaattacag aactattggt gtttctgctg ctgctagata caatcaatgt aatactacta    60
gaggtaatga ag                                                       72

<210> SEQ ID NO 13
<211> LENGTH: 74
<212> TYPE: DNA
<213> ORGANISM: Artificial Sequence
<220> FEATURE:
<223> OTHER INFORMATION: Primer

<400> SEQUENCE: 13
agtaacaaca ccaacagcct taccagcctt cttagctcta ttaataacag aagtaacttc    60
attacctcta gtag                                                     74

<210> SEQ ID NO 14
<211> LENGTH: 74
<212> TYPE: DNA
<213> ORGANISM: Artificial Sequence
<220> FEATURE:
<223> OTHER INFORMATION: Primer

<400> SEQUENCE: 14

```
gctgttggtg ttgttactac tactagagtt caacatgctt ctccagctgg tgcttacgct    60
catactgtta atag                                                      74

<210> SEQ ID NO 15
<211> LENGTH: 68
<212> TYPE: DNA
<213> ORGANISM: Artificial Sequence
<220> FEATURE:
<223> OTHER INFORMATION: Primer

<400> SEQUENCE: 15
caaccattct tttgagcatc agctggcaaa tcagcatcag agtaccaatt tctattaaca    60
gtatgagc                                                             68

<210> SEQ ID NO 16
<211> LENGTH: 55
<212> TYPE: DNA
<213> ORGANISM: Artificial Sequence
<220> FEATURE:
<223> OTHER INFORMATION: Primer

<400> SEQUENCE: 16
gatgctcaaa agaatggttg tcaagatatt gctgctcaat tggtttacaa tatgg         55

<210> SEQ ID NO 17
<211> LENGTH: 72
<212> TYPE: DNA
<213> ORGANISM: Artificial Sequence
<220> FEATURE:
<223> OTHER INFORMATION: Primer

<400> SEQUENCE: 17
ccttctggaa acatgtacat tctaccacca cccaaaataa catcaatatc catattgtaa    60
accaattgag ca                                                        72

<210> SEQ ID NO 18
<211> LENGTH: 71
<212> TYPE: DNA
<213> ORGANISM: Artificial Sequence
<220> FEATURE:
<223> OTHER INFORMATION: Primer

<400> SEQUENCE: 18
gtacatgttt ccagaaggta ctccagatcc agaataccca gatgatgctt ctgttaatgg    60
tgttagaaag g                                                         71

<210> SEQ ID NO 19
<211> LENGTH: 73
<212> TYPE: DNA
<213> ORGANISM: Artificial Sequence
<220> FEATURE:
<223> OTHER INFORMATION: Primer

<400> SEQUENCE: 19
catattgagc accttgatgc ttagcttgcc attcttgaac caaattttgc ttatcctttc    60
taacaccatt aac                                                       73

<210> SEQ ID NO 20
<211> LENGTH: 71
<212> TYPE: DNA
<213> ORGANISM: Artificial Sequence
<220> FEATURE:
<223> OTHER INFORMATION: Primer
```

```
<400> SEQUENCE: 20
gcatcaaggt gctcaatatg tttggaatag aactgctttg ttgcaagctg ctgatgattc    60
tagtgttact c                                                         71

<210> SEQ ID NO 21
<211> LENGTH: 54
<212> TYPE: DNA
<213> ORGANISM: Artificial Sequence
<220> FEATURE:
<223> OTHER INFORMATION: Primer

<400> SEQUENCE: 21
cttcatatca gctggttcaa acaaacccat caaatgagta acactagaat catc          54

<210> SEQ ID NO 22
<211> LENGTH: 59
<212> TYPE: DNA
<213> ORGANISM: Artificial Sequence
<220> FEATURE:
<223> OTHER INFORMATION: Primer

<400> SEQUENCE: 22
gaaccagctg atatgaagta taatgttcaa caagatcata ctaaggatcc aactttggc     59

<210> SEQ ID NO 23
<211> LENGTH: 67
<212> TYPE: DNA
<213> ORGANISM: Artificial Sequence
<220> FEATURE:
<223> OTHER INFORMATION: Primer

<400> SEQUENCE: 23
cctcttggat ttctagacaa aacttgcaaa gcagcttcag tcatttcagc caaagttgga    60
tccttag                                                              67

<210> SEQ ID NO 24
<211> LENGTH: 69
<212> TYPE: DNA
<213> ORGANISM: Artificial Sequence
<220> FEATURE:
<223> OTHER INFORMATION: Primer

<400> SEQUENCE: 24
gtctagaaat ccaagaggtt tttacttgtt tgttgaaggt ggtagaattg atcatggtca    60
tcatgatgg                                                            69

<210> SEQ ID NO 25
<211> LENGTH: 73
<212> TYPE: DNA
<213> ORGANISM: Artificial Sequence
<220> FEATURE:
<223> OTHER INFORMATION: Primer

<400> SEQUENCE: 25
ccttagcaat agcattatca aacataatag cttcagtcaa agccatataa gccttaccat    60
catgatgacc atg                                                       73

<210> SEQ ID NO 26
<211> LENGTH: 74
<212> TYPE: DNA
<213> ORGANISM: Artificial Sequence
<220> FEATURE:
```

```
<223> OTHER INFORMATION: Primer

<400> SEQUENCE: 26
gataatgcta ttgctaaggc taatgaattg acttctgaat tggatacttt gattttggtt      60
actgctgatc atag                                                        74

<210> SEQ ID NO 27
<211> LENGTH: 73
<212> TYPE: DNA
<213> ORGANISM: Artificial Sequence
<220> FEATURE:
<223> OTHER INFORMATION: Primer

<400> SEQUENCE: 27
ccaaaccaaa aatagaagta cctctcaaag tgtaaccacc aaaagaaaaa acatgactat      60
gatcagcagt aac                                                         73

<210> SEQ ID NO 28
<211> LENGTH: 73
<212> TYPE: DNA
<213> ORGANISM: Artificial Sequence
<220> FEATURE:
<223> OTHER INFORMATION: Primer

<400> SEQUENCE: 28
cttctatttt tggtttggct ccaggtaagg ctttggatag taagtcttac acttctattt      60
tgtatggtaa tgg                                                         73

<210> SEQ ID NO 29
<211> LENGTH: 76
<212> TYPE: DNA
<213> ORGANISM: Artificial Sequence
<220> FEATURE:
<223> OTHER INFORMATION: Primer

<400> SEQUENCE: 29
ctagtactac cattaacatc tggtctagaa ccaccaccca agcataacc tggaccatta       60 ccatacaaaa tagaag                                                      76

<210> SEQ ID NO 30
<211> LENGTH: 77
<212> TYPE: DNA
<213> ORGANISM: Artificial Sequence
<220> FEATURE:
<223> OTHER INFORMATION: Primer

<400> SEQUENCE: 30
gatgttaatg gtagtactag tgaagaacca tcttacagac aacaagctgc tgttccattg      60
gctagtgaaa ctcatgg                                                     77

<210> SEQ ID NO 31
<211> LENGTH: 73
<212> TYPE: DNA
<213> ORGANISM: Artificial Sequence
<220> FEATURE:
<223> OTHER INFORMATION: Primer

<400> SEQUENCE: 31
caccatgaac caaatgagct tgtggacctc tagcaaaaac agcaacatct tcaccaccat      60
gagtttcact agc                                                         73
```

```
<210> SEQ ID NO 32
<211> LENGTH: 74
<212> TYPE: DNA
<213> ORGANISM: Artificial Sequence
<220> FEATURE:
<223> OTHER INFORMATION: Primer

<400> SEQUENCE: 32
gctcatttgg ttcatggtgt tcaagaagaa acttttgttg ctcatattat ggcttttgct      60
ggttgtgttg aacc                                                       74

<210> SEQ ID NO 33
<211> LENGTH: 82
<212> TYPE: DNA
<213> ORGANISM: Artificial Sequence
<220> FEATURE:
<223> OTHER INFORMATION: Primer

<400> SEQUENCE: 33
gcgcggtacc ttaatctgga atactagtag cagtagctgg agctggcaaa ttacaatcag      60
tgtatggttc aacacaacca gc                                              82

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
gcgcgcctag gagatctaac atccaaagac g                                    31

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
cgcgcgctag cggatccgca caaacgaag                                       29

<210> SEQ ID NO 36
<211> LENGTH: 10
<212> TYPE: PRT
<213> ORGANISM: Saccharomyces cerevisiae

<400> SEQUENCE: 36

Glu Ala Glu Ala Glu Phe Leu Ile Pro Ala
 1               5                  10

<210> SEQ ID NO 37
<211> LENGTH: 4
<212> TYPE: PRT
<213> ORGANISM: Saccharomyces cerevisiae

<400> SEQUENCE: 37

Leu Ile Pro Ala
 1

<210> SEQ ID NO 38
<211> LENGTH: 6
<212> TYPE: PRT
<213> ORGANISM: Saccharomyces cerevisiae
```

```
-continued

<400> SEQUENCE: 38

Glu Ala Glu Ala Glu Phe
1               5
```